(12) United States Patent
Schaible et al.

(10) Patent No.: US 7,641,838 B2
(45) Date of Patent: Jan. 5, 2010

(54) CATHETER WITH A TRANSPARENT SHAFT

(75) Inventors: Stephen G. Schaible, Anaheim, CA (US); Timoteo J. Tomas, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 896 days.

(21) Appl. No.: 11/201,994

(22) Filed: Aug. 10, 2005

(65) Prior Publication Data

US 2006/0184110 A1 Aug. 17, 2006

Related U.S. Application Data

(62) Division of application No. 09/458,354, filed on Dec. 9, 1999, now Pat. No. 6,942,648.

(51) Int. Cl.
*B29C 59/00* (2006.01)

(52) U.S. Cl. ...................................... 264/293

(58) Field of Classification Search ................ 264/146, 264/150, 173, 139, 293; 425/133.1, 131.1; 606/191–194; 604/96.01, 101.01, 523, 264
See application file for complete search history.

(56) References Cited

U.S. PATENT DOCUMENTS

| 4,963,306 | A | 10/1990 | Weldon |
| 5,139,496 | A | 8/1992 | Hed |
| 5,188,596 | A | 2/1993 | Condon et al. |
| 5,221,728 | A | 6/1993 | Bennett et al. |
| 5,270,086 | A | 12/1993 | Hamlin |
| 5,312,376 | A | 5/1994 | Van Heugten |
| 5,316,706 | A | 5/1994 | Muni et al. |
| 5,344,400 | A | 9/1994 | Kaneko et al. |
| 5,411,016 | A | 5/1995 | Kume et al. |
| 5,496,271 | A | 3/1996 | Burton et al. |
| 5,554,121 | A | 9/1996 | Ainsworth et al. |
| 6,104,530 | A | 8/2000 | Okamura et al. |

FOREIGN PATENT DOCUMENTS

EP 0 452 595 10/1991

*Primary Examiner*—Manuel A Mendez
(74) *Attorney, Agent, or Firm*—Fulwider Patton LLP

(57) ABSTRACT

An intraluminal catheter having at least a section of the catheter shaft being relatively transparent, and the method of manufacture thereof. In a presently preferred embodiment, the intraluminal catheter is a balloon catheter having a transparent shaft section formed of a polyetheretherketone polymeric material. The substantially transparent shaft section, of the catheter, is amorphous, and is substantially free of water marks and gels that would limit the transparency.

7 Claims, 2 Drawing Sheets

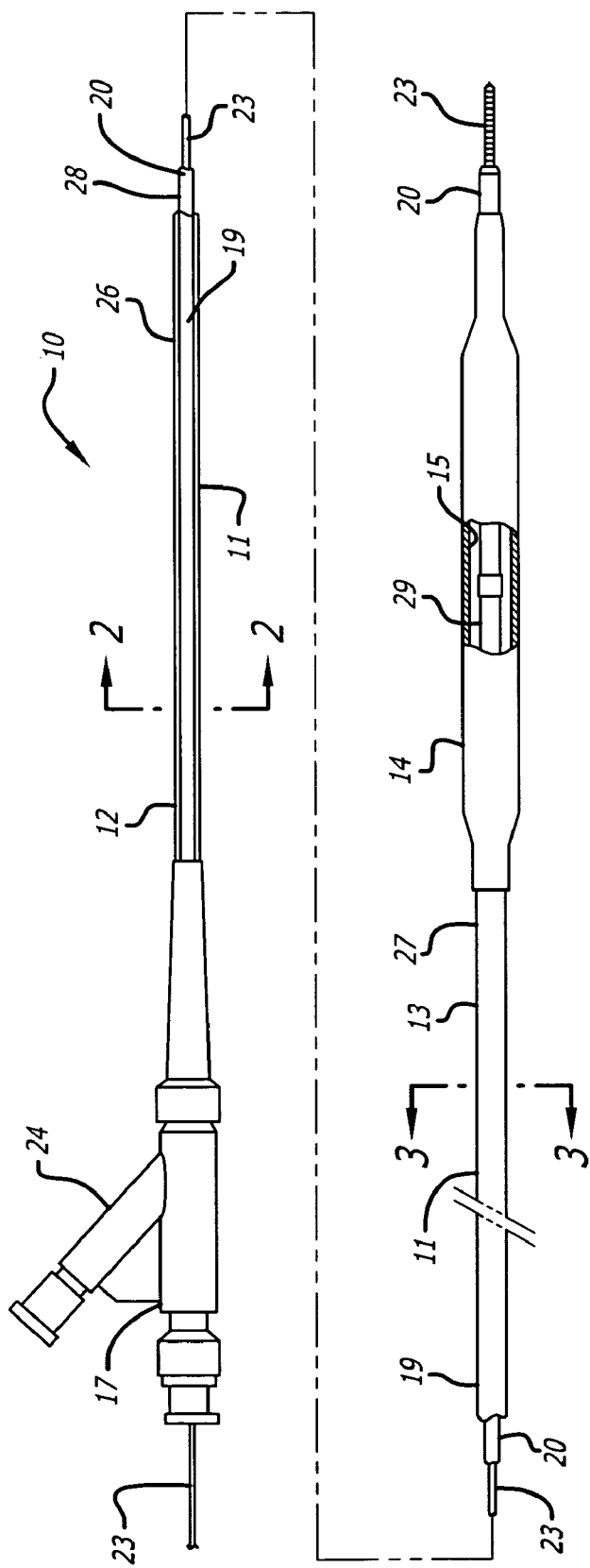
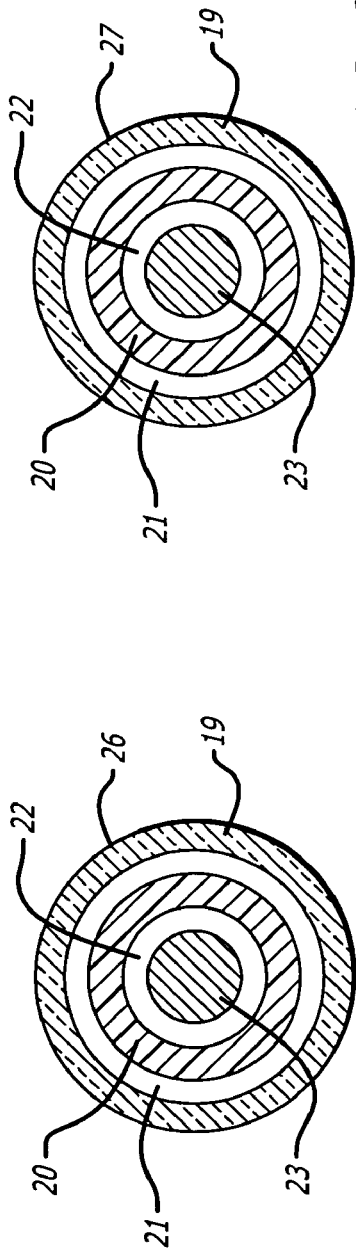
FIG. 1
FIG. 2
FIG. 3

CATHETER WITH A TRANSPARENT SHAFT

This application is a divisional of U.S. patent application Ser. No. 09/458,354, filed Dec. 9, 1999, which issued as U.S. Pat. No. 6,942,648 on Sep. 13, 2005.

BACKGROUND OF THE INVENTION

This invention generally relates to intraluminal catheters, such as balloon dilatation catheters used in percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery until the balloon on the catheter is disposed within the stenotic region of the patient's artery. The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom.

Commercially available balloon catheters for angioplasty and other intravascular procedures usually comprise an elongated shaft with an inflatable dilatation member on a distal portion of the shaft and an adapter on the proximal end of the shaft for the delivery of inflation fluid through an inner lumen extending through the catheter shaft to the interior of the inflatable dilatation member. Additionally, a guidewire lumen may be provided along at least a section of the elongated shaft. The elongated shaft typically comprises a relatively stiff proximal shaft section and a relatively flexible distal shaft section to facilitate catheter maneuverability and, therefore, the ability to effectively position the catheter at a desired location within a patient. Generally, angioplasty catheter proximal shaft sections are made highly crystalline or semi-crystalline in order to increase the strength and stiffness of the shaft section.

Polymeric tubular catheter components are typically formed by extrusion, although they may be made by a variety of methods depending on the material used and the desired characteristics of the component. For example, a catheter shaft may be formed by free extrusion, wherein melted polymeric material passes through an extrusion die over a mandrel. Upon exiting the extruder, the tube is typically passed into a quench bath. The wall thickness of an extruded tube is a function of the annular gap between the die and the mandrel, and post extrusion processing such as draw-down of the polymeric material. Draw-down is the ratio of the die diameter to the final diameter of the extruded article, and is therefore a measure of the thinning of the extruded article as it exits the extruder. Where a multi-layered article is desired, the layers may be co-extruded, or a second layer extruded over an existing polymeric tube.

It would be a significant advance to provide a catheter having a polymeric shaft that is substantially transparent. The present invention satisfies these and other needs.

SUMMARY OF THE INVENTION

The invention is directed to an intraluminal catheter having a catheter shaft which is substantially transparent along at least a portion thereof, and the method of manufacture thereof. In a presently preferred embodiment, the intraluminal catheter is a balloon catheter having a transparent shaft section formed of a polyetheretherketone polymeric material. The transparency of the shaft is the result of an extrusion process which produces an amorphous extrudate, and which minimizes the formation of gels and watermarks which would otherwise reduce the transparency of the extrudate.

In a method of the invention, the presence of gels which would cloud the extruded polymeric shaft are minimized by maintaining the temperature within the extruder above the temperature at which gels typically form in the polymer. Additionally, the polymeric material within the extruder is passed through one or more filtration screens, and preferably at least two filtration screens, having a mesh size which is preferably about 18 μm, to filter any gels that do form.

The polymeric tubing is extruded and passed into a quench bath, so that it is formed in its amorphous state. In a method of the invention, the crystallization of the polymeric material is minimized by limiting the time at which the extrudate is at or above the material's crystallization temperature. Additionally, water marks, which would otherwise form on the extrudate during the quenching process and limit the transparency thereof, are minimized. The extrudate which exits the extruder and contacts the quench medium is at a relatively low temperature, and the quench medium resists boiling during the quenching process. Consequently, the resulting extruded polymeric tubing is substantially free of water marks.

In a presently preferred embodiment polyetheretherketone (PEEK) is the polymeric material which forms the transparent shaft section. The amorphous PEEK provides a shaft section having in addition to transparency, high strength and stiffness needed for pushability and torqueability. Other polymeric materials suitable for use in the method of the invention to form the transparent shaft include polyphenylene sulfide (PPS), and polyether sulfone (PES), which, similar to PEEK, are semi-crystalline with a relatively high crystallization temperature which is between the melting temperature and the temperature at which the polymeric material solidifies.

The balloon catheter of the invention generally comprises a catheter having an elongated shaft with an inflatable balloon. Various designs for balloon catheters well known in the art may be used in the catheter of the invention. For example, the catheter may be a conventional over-the-wire dilatation catheter for angioplasty having a guidewire receiving lumen extending the length of the catheter shaft from a guidewire port in the proximal end of the shaft, or a rapid exchange dilatation catheter having a short guidewire lumen extending to the distal end of the shaft from a guidewire port located distal to the proximal end of the shaft. In a presently preferred embodiment of the invention, the transparent shaft section formed of PEEK is the proximal shaft section, and preferably the proximal shaft section of an outer tubular member, so that the physician can see the presence of elements, such as the inner tubular member or inflation fluid, within the outer tubular member lumen. Additionally, an inner tubular member having a transparent shaft section allows the physician to observe a guidewire within the inner tubular member lumen.

The balloon catheter of the invention has a shaft section that is transparent due to the amorphous nature of the polymer and the absence of gels and water marks that would otherwise limit the transparency of the shaft. When used to form the proximal shaft section of a balloon catheter outer tubular member, the transparency of the shaft section allows the physician to see the presence of elements therein. Moreover, a transparent shaft section formed of polyetheretherketone nonetheless has sufficient strength and stiffness to form a proximal shaft section that transmits torque and push, to maneuver the distal end of the catheter within the patient. These and other advantages of the invention will become more apparent from the following detailed description of the invention and the accompanying exemplary drawings.

BRIEF DESCRIPTION OF THE DRAWINGS

FIG. 1 is an elevational view partially in section of a catheter which embodies features of the invention showing the balloon in an unexpanded state.

FIG. 2 is a transverse cross sectional view of the catheter of FIG. 1 taken along lines 2-2.

FIG. 3 is a transverse cross sectional view of the catheter of FIG. 1 taken along lines 3-3.

DETAILED DESCRIPTION OF THE INVENTION

Figure 4:
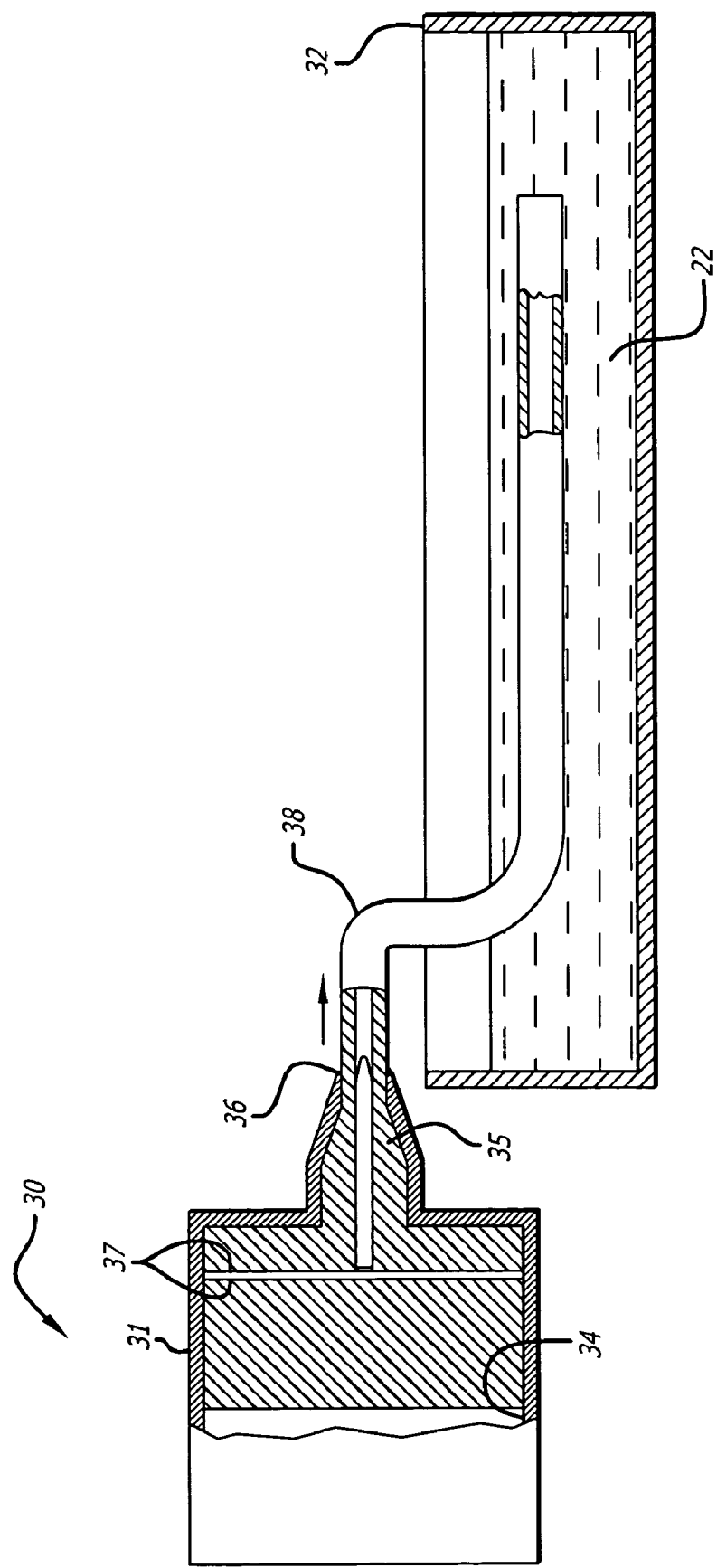
FIG. 4 is a schematic illustration of an apparatus used in the method of the invention.

As shown in FIG. 1, an intraluminal catheter 10 which embodies features of the invention generally includes an elongated catheter shaft 11 having a proximal section 12 and distal section 13, an inflatable balloon 14, on the distal section 13 of the catheter shaft 11, and an adapter 17 mounted on the proximal section 12 of shaft 11 to direct inflation fluid to the interior of the inflatable balloon 14. FIGS. 2 and 3 illustrate transverse cross sections of the catheter shown in FIG. 1, taken along lines 2-2 and 3-3 respectively.

The intraluminal catheter 10 shown in FIG. 1 is an over-the-wire catheter, and is illustrated with the balloon 14 in an unexpanded state. The catheter shaft 11 has an outer tubular member 19 and an inner tubular member 20 disposed within the outer tubular member and defining, with the inner walls of the outer tubular member 19, inflation lumen 21. Inflation lumen 21 is in fluid communication with the interior chamber 15 of the inflatable balloon 14. The inner tubular member 20 has an inner lumen 22 extending therein, which is configured to slidably receive a guidewire 23 suitable for advancement through a patient's vessels, such as the coronary arteries. FIG. 2, showing a transverse cross section of the catheter shaft 11 of FIG. 1, illustrates guidewire receiving lumen 22 and inflation lumen 21. The outer tubular member 19 has a proximal shaft section 26 and a distal shaft section 27, and the inner tubular member 20 has a proximal shaft section 28 and a distal shaft section 29. The distal extremity of inflatable balloon 14 is sealingly secured to the inner tubular member distal shaft section 29, and the proximal extremity of the balloon 14 is sealingly secured to the outer tubular member distal shaft section 27. The balloon 14 can be inflated by radiopaque fluid from an inflation port 24 through inflation lumen 21 contained in the catheter shaft 11. The details and mechanics of balloon inflation vary according to the specific design of the catheter, and are well known in the art.

In the embodiment illustrated in FIG. 1, the outer tubular member 19 proximal shaft section 26, formed using the method of the invention, is substantially transparent. The inner tubular member 20 within the outer tubular member 19 is visible through the outer tubular member proximal shaft section 26.

A method of the present invention provides an extruded polymeric catheter shaft that is substantially transparent. An extrusion apparatus 30 useful in a method of the invention is illustrated schematically in FIG. 4, and includes an extruder 31, and a quench bath 32 having quench medium 33 therein. The extruder comprises a barrel 34, which contains the molten polymeric material, a cross-head or die 35 which shapes the polymeric material into a tube, and an exit 36. Typically, the temperature of the polymeric material is controlled at a number of locations within the extruder. In one method of the present invention, the temperature at the end of the die 35 at the extruder exit 36 is controlled to such a degree that the crystallinity, and gel and water mark formation within the extrudate are minimized.

In a method of the present invention, a polymeric material is melt processed within extrusion apparatus 30 so that the temperature of the polymeric material at the end of the die 35 at the extruder exit 36 is within the lower melt process temperature range of the polymer. Specifically, the temperature at the end of the die 35 is not more than about 5% to about 15% greater than the melting point of the polymer, and preferably not more than about 10% to about 13% greater than said melting point. PEEK may generally be melt processed at about 645° F., the melting point of PEEK, to about 800° F., above which PEEK thermally degrades. In the presently preferred embodiment in which the polymeric material used to form the substantially transparent shaft section is PEEK, the temperature in the extruder is from about 720° F. to about 730° F., i.e., 11.5% to about 13% above the melting point of PEEK.

Within the extruder 31, the polymeric material is passed through preferably at least two filtration screens 37, so that any gels that do form are removed by the screen. The filtration screens 37 have a mesh size of about 10 µm to about 30 µm, and preferably about 18 µm, depending on the nature of the polymer, amount of gel, and degree of visual clarity desired in the extrudate. The polymeric material is passed out the exit 36 in the extruder 31 to form extruded tubing 38. The extruded tubing is then introduced into the quench bath 32 and quench medium 33 therein, to thereby cool the extruded polymer tubing. Typically, the extruded tubing 38 is in ambient air as it passes from the extruder exit 36 to the quench bath 32, however, the atmosphere or temperature between the extruder exit 36 and quench bath may be controlled if desired. In an embodiment of the invention, the quench medium 33 will not boil upon the introduction of the extruded tubing 38 from the extruder 31, so that water marks which would otherwise form on the extrudate are minimized or prevented. In a presently preferred embodiment, the quench medium 33 is chilled water, which is preferably from about 4° C. to about 25° C., and most preferably about 10° C. However, other suitable quench media exist including high boiling point substances, such as propylene glycol, which are water soluble and non-toxic. Additionally, high boiling point substances such as oil may be used as the quench medium, provided the extruded tubing is cleaned to remove any oil residues thereon.

In one embodiment of the invention, the quench bath 32 is spaced about 3 mm to about 30 mm, and preferably about 13 mm, from the extruder 31 exit, so that the extruded tubing is maintained between the extruder and the quench bath for about 0.01 sec to about 0.10 sec after exiting the extruder and before contacting the quench medium. Consequently, the time during which the extruded tubing is above the crystallization temperature of the polymeric material is limited, to thereby limit the crystallinity of the extruded tubing and produce an amorphous shaft section. Alternatively, the time during which the extruded tubing is above the crystallization temperature can be minimized by increasing the flow rate of the extrudate exiting the extruder. Additionally, employing the relatively low temperature of the lower melt process temperature range to melt process the polymeric material limits the crystallinity and water marks in the extruded tubing.

In accordance with the invention the substantially transparent shaft section 26, of the catheter 10 shown in FIG. 1, is amorphous, and is substantially free of any water marks and gels that would limit the transparency. The transparent shaft section 26 has a percent transmittance of light in the visible wavelengths of about 50% to about 100% through the dual wall thickness of the shaft section 26. The percent crystallinity of the transparent shaft section 26 is about 0% to about 20%, and typically about 2%. In a presently preferred embodiment, the transparent shaft section 26 is formed from PEEK polymeric material. The transparent proximal shaft section 26 of the outer tubular member is pushable and torqueable.

In the embodiment illustrated in FIG. 1, the catheter 10 outer tubular member 19 has a transparent proximal shaft section 26 and a distal shaft section 27. The length of the transparent proximal shaft section 26 is about 50 cm to about 100 cm, and typically about 75 cm for PTCA, and the length of the distal shaft section 27 is about 10 cm to about 40 cm, and typically about 30 cm for PTCA. The length of the catheter 10 may be about 90 to about 150 cm, and typically about 135 cm for PTCA. In another embodiment, the outer tubular member 19 amorphous transparent proximal shaft section 26 is formed of PEEK, and the distal shaft section 27 is formed of a different polymeric material, such as polyamide, polyetheramide, and polyetherester. The shaft sections 26 and 27, may be joined by a variety of suitable means such as at a lap joint formed by heat or laser fusion or commercially available adhesives, e.g. cyanoacrylate adhesives, or other means known to those of ordinary skill in the art. Alternatively, the outer tubular member 19 comprises an amorphous transparent proximal shaft section 26 and a semicrystalline distal shaft section 27 formed as a unitary extrusion of the same polymeric material. The semicrystalline shaft section has a crystallinity of about 25 percent to about 75 percent.

The outer tubular member 19 has an outer diameter (OD) of about 0.03 to about 0.05 inch (0.76-1.27 mm) and an inner diameter (ID) of about 0.02 to about 0.035 inch (0.508-0.899 mm). The outer tubular member 19 may taper in its distal portion to a smaller OD of about 0.04 to about 0.02 inch (1.02-0.508 mm) and a smaller ID of about 0.03 to a bout 0.015 inch (0.762-0.381 mm). The smaller diameter portion between the taper and the proximal extremity of the balloon may be about 5 to about 15 cm in length.

The inner tubular member 20 has an OD from about 0.014 to about 0.026 inch (0.356-0.66 mm). The ID of the inner tubular member 20 will usually be determined by the diameter of the guidewire which is to be used with the catheter, which may range from about 0.008 to about 0.02 inch (0.203-0.51 mm). The diameter of the inner tubular member lumen should be about 0.002 to about 0.005 inch (0.051-0.127 mm) larger than the OD of the guidewire.

The length of the balloon 14 may be about 0.5 cm to about 6 cm, preferably about 1.0 cm to about 4.0 cm. After being formed, the outer diameter of the balloon at nominal pressure (e.g. 6-8 ATM) is generally about 1 mm to about 4 m, and typically about 3 mm, although balloons having an outer diameter of about 1 cm may also be used. The single wall thickness is about 0.0004 in (0.0102 mm) to about 0.01 in (0.25 mm), and typically about 0.0015 in (0.0381 mm) to about 0.005 inches (0.13 mm), and more specifically about 0.0006 in (0.0152 mm). In the embodiment in which the coexfusion balloon has two layers, the inner layer single wall thickness is about 0.0003 in (0.0076 mm) to about 0.0006 in (0.0152 mm), and the outer layer is about 0.0002 in (0.0051 mm) to about 0.0005 in (0.0127 mm).

It will be apparent from the foregoing that, while particular forms of the invention have been illustrated and described, various modifications can be made without departing from the spirit and scope of the invention. For example, while the balloon catheter illustrated in FIG. 1 has inner and outer tubular members with independent lumens, a single tubular membered shaft having two lumens therein may also be used. Additionally, while the transparent catheter shaft section is discussed in terms of a proximal shaft section, other shaft sections may comprise the transparent shaft section. Other modifications may be made without departing from the scope of the invention.

What is claimed is:

1. A method of making a substantially transparent catheter shaft, comprising:
   a) passing melted polymeric material through at least one filtration screen to filter the polymeric material;
   b) extruding the filtered molten polymeric material through a die of an extruder to form extruded tubing;
   c) maintaining a temperature at an exit of the extruder no greater than from about 5% to about 15% above a melting point of the polymeric material; and
   d) introducing the extruded tubing into a quench bath containing a quench medium, and contacting the extruded tubing with the quench medium, and so that the polymeric material forming the extruded tubing is in an amorphous state.

2. The method of claim 1 wherein step a comprises passing the melted polymeric material through at least two filtration screens having a mesh size of from about 10 μm to about 30 μm.

3. The method of claim 1 including maintaining the extruded tubing between the extruder exit and the quench bath for about 0.01 sec to about 0.10 sec after exiting the extruder and before contacting the quench medium.

4. The method of claim 1 wherein the polymeric material is a poly-etheretherketone polymeric material, and including melt processing the polyetheretherketone polymeric material at a temperature of from about 720° F. to about 730° F.

5. The method of claim 1 including minimizing the formation of water marks on the tubing by providing a quench medium which does not boil upon introduction of the tubing therein.

6. The method of claim 1 including providing a quench medium comprising propylene glycol.

7. The method of claim 1 including providing an aqueous quench medium, and chilling the aqueous quench medium to about 4° C.

* * * * *